United States Patent [19]
von Blücher et al.

[11] Patent Number: 5,695,775
[45] Date of Patent: Dec. 9, 1997

[54] DECONTAMINATING OF SKIN OR MATERIALS CONTAMINATED BY CHEMICAL WARFARE AGENTS

[75] Inventors: Hasso von Blücher, Parkstrasse 10, D-40699 Erkrath; Ernest de Ruiter, Höhenstrasse 57a, D-51381 Leverkusen, both of Germany; Jan Medema, Benthuizen, Netherlands

[73] Assignees: Hasso von Blücher, Erkrath; Ernest de Ruiter, Leverkusen, both of Germany

[21] Appl. No.: 513,093

[22] Filed: Aug. 9, 1995

[30] Foreign Application Priority Data

Aug. 13, 1994 [DE] Germany ............ 44 28 793.3
Jun. 14, 1995 [DE] Germany ............ 195 21 679.2

[51] Int. Cl.$^6$ ............ C11D 1/20; C11D 1/02; C06D 7/00; C01B 17/00
[52] U.S. Cl. ............ 424/405; 422/28; 422/1
[58] Field of Search ............ 588/200; 424/405; 422/1, 28

[56] References Cited

U.S. PATENT DOCUMENTS

| | | | |
|---|---|---|---|
| 2,222,370 | 11/1940 | Mori | 252/70 |
| 4,146,499 | 3/1979 | Rosano | 252/186 |
| 4,439,337 | 3/1984 | Nimerick et al. | 252/70 |
| 4,744,917 | 5/1988 | Scardera | 252/187 |
| 4,784,699 | 11/1988 | Cowsar | 134/42 |
| 4,949,641 | 8/1990 | Sayles | 102/293 |
| 5,387,717 | 2/1995 | Puckett et al. | 564/295 |

*Primary Examiner*—Thurman K. Page
*Assistant Examiner*—M. Sikha
*Attorney, Agent, or Firm*—Cohen, Pontani, Lieberman & Pavane

[57] ABSTRACT

The present invention relates to a process for the decontamination of chemical warfare agents which are present on the skin or have penetrated below the surface into the skin, or materials contaminated therewith, by a micro-emulsion which contains a $C_8$–$C_{14}$ alkane, an anionic surfactant, an aliphatic $C_3$–$C_{10}$ alcohol, and water, and to which possibly a wetting agent and/or antifreeze components such as antifreeze agents, NaCl or $CaCl_2$ are also added.

14 Claims, No Drawings

DECONTAMINATING OF SKIN OR MATERIALS CONTAMINATED BY CHEMICAL WARFARE AGENTS

The present invention relates to the use of a micro-emulsion for the decontaminating of chemical warfare agents which adhere to the skin or have penetrated the surface of the skin or of materials contaminated with them.

With the introduction of chemical warfare agents, there arose, at the same time, the need for protection, and also the need for a possibility of decontaminating both contaminated persons and contaminated materials and objects, i.e. of washing off or destroying the adhering warfare agents. Objects to be decontaminated range from protective masks to airplanes. In principle, a distinction is to be made between chemical methods, which are based primarily on oxidation or hydrolysis, and physical methods, in which, for instance, a soap, water and solvent are used. The decontamination of, for instance, permeable protective clothing which always contains activated charcoal, furthermore requires relatively high temperatures in order to desorb the warfare agents from the carbon.

The demands made on a method of decontamination can be summarized as follows:

1. The objects treated should not experience any damage.
2. The decontaminating agent should be environmentally friendly and non-toxic to man.
3. The products used should not be easily inflammable by themselves or in the mixture used.
4. It should be possible to use them under all conceivable circumstances, even with regard to the temperature (−20° C. to 55° C.).
5. The individual components should have high stability upon storage, and the ready-to-use mixture should possess good stability.
6. The logistical problems should be as few as possible.
7. The products used should be available commercially and be inexpensive.

These requirements are at present merely desiderate in the case of the agents used today in NATO, such as, for instance, the so-called C8-emulsion, which are based on calcium chloride or calcium hypochlorite. Although the warfare agents are destroyed in these processes, and their use is relatively simple and the products are of low cost, oxidative decontamination processes are very corrosive and can therefore not be used, for instance, on airplanes, sensitive devices (for instance radio equipment), interiors of motor vehicles, etc.; they easily dissolve fresh alkyd-resin paints, are not always sufficiently active against poisons which have penetrated deeply, and the chemicals used are neither environmentally friendly nor easy to store.

The above-mentioned C8-emulsion has the following composition:

7.5% calcium hypochlorite
15% perchlorethylene or carbon tetrachloride
1% emulsifier
76.5% water In the USA and many Western countries there is furthermore used, for instance, DS2 solution which cannot be diluted with water and can be considered extremely corrosive due to its chemical composition (2% concentrated sodium hydroxide solution, 70% diethylenetriamine and 28% ethylene glycol monomethyl ester) and also highly inflammable.

The object of the present invention is to provide a process of decontamination in which the decontaminating agent used avoids the disadvantages of these very aggressive and corrosive solutions or emulsions.

The present invention provides a process for the decontamination of chemical warfare materials which are present on the skin or have penetrated from the surface into the skin, or of materials contaminated therewith. For purposes of the present invention, the word "subject" shall mean a person or thing used or treated in a specified way. Thus, the micro-emulsion of the present invention can be used to treat a subject, i.e. both animate and/or inanimate objects, containing the contaminated material on the surface thereof or having absorbed same. In accordance with the process of the invention, a micro-emulsion which is free of hypochlorite is used, it extracting or removing the warfare substances, which therefore is a physical process. The warfare substances are washed off in high dilution and destroyed—even without specific chemical destruction—after some time degraded by hydrolysis, whether in the ground or in collecting containers. Chemical decomposition or destruction of the warfare substances, for instance by calcium chloride can also, of course, be effected in these containers.

Emulsions are present when an oil phase is dispersed in an aqueous phase, or vice versa. In this connection, the droplets generally have a diameter of 1–10 µm. Emulsions have a free energy which is proportional to the surface between the phases. The finer the emulsion, the greater the free energy. Energy (stirring, shaking) is therefore required for the preparation of an emulsion. Emulsions, therefore, are not thermodynamically stable; they tend to form coarser and coarser emulsions since the interphase surface is thereby reduced. The growth of the droplets takes place by coalescence or mass transport. This coalescence of the droplets can be prevented by the addition of emulsifiers or stabilizers. The latter are at the same time oleophilic and hydrophilic and cover the droplets with a protective skin. In contradistinction to conventional emulsions, micro-emulsions are only slightly cloudy, which is the result of the much smaller droplets (60–200 Å). The most important difference, however, is that they are thermodynamically stable and that their production does not require any additional energy (for instance, stirring). Their properties are independent of the method of their production. Ordinarily, ionic wetting agents such as, for instance, soaps, together with non-ionic "co-surfactants" which are in general a higher alcohol, are required.

The micro-emulsion used in accordance with the invention contains a $C_8$–$C_{14}$ alkane as oil phase (for instance, n-dodecane), an anionic surfactant as emulsifier (for instance, the alkali salt of a fatty acid or a sulfonated hydrocarbon such as, for instance, sodium lauryl sulfate SDS), an aliphatic $C_3$–$C_{10}$ alcohol as co-emulsifier (also known as co-tenside or "co-surfactant", for instance 1-hexanol), and a large amount of water. All components are readily biologically degradable and satisfy modern requirements with respect to the protection of the environment. Rinsing with water is to be sure desirable but by no means necessary.

The micro-emulsion used in accordance with the invention has the following composition, the percentages referring to the total weight of the micro-emulsion:

0.1–3.5% $C_8$–$C_{14}$ alkane
0.5–4.0% anionic surfactant
0.5–7.0% aliphatic $C_3$–$C_{10}$ alcohol
Balance water 0.1 to 6.0% of one or more wetting agents can possibly be added to the micro-emulsion. As wetting agent, FSO-100 (DuPont), a typical wetting agent of the so-called zonyl family, is for instance used. Another wetting agent which can be used is, for instance, TX-100, which is an ionic wetting agent and permits the use of salt-containing water such as, for instance sea water, since it makes the micro-emulsion insensitive to salt water or stabilizes it; TX-100, the abbreviation for Triton® X-100, is polyethylene glycol mono[p-(1,1,3,3-tetramethylbutyl)-phenyl] ether, also known as t-octylphenoxypolyethoxyethanol, which is sold, for instance, by MERCK. In the case of an NaCl content of 3.5% (for instance, sea water), 4% TX-100 is preferably added to the solution.

In order to increase the resistance to freezing there can also be added to the micro-emulsion an antifreeze agent and/or NaCl or $CaCl_2$. By antifreeze agent there are understood all commercial antifreeze or freeze-protection agents, for instance ones having a base of glycols, such as, for instance ethylene glycol or propylene glycol, glycerol, 2-propanol, etc.

Preferred components for the micro-emulsion are n-dodecane as oil phase, the alkali salt of a fatty acid or of a sulfonated hydrocarbon such as, for instance, sodium lauryl sulfate (SDS) as emulsifier, 1-hexanol as co-emulsifier, and FSO-100 (DuPont) as wetting agent.

The guide recipes for the micro-emulsion which are indicated in the following indicate what compositions are considered optimal for most cases. In this connection, not only the absolute quantities but also the ratio of the components have an influence. These guide recipes are therefore not to be considered limitative, since the person skilled in the art, once noting the teaching of the present invention, can vary each component within given limits in any order possible to obtain even better results in special cases.

A typical formulation of the micro-emulsion is:

0.7% n-dodecane as $C_8$–$C_{14}$ alkane (oil phase)

2.1% SDS (sodium lauryl sulfate) as anionic surfactant (emulsifier)

2.9% 1-hexanol as aliphatic $C_3$–$C_{10}$ alcohol (co-emulsifier)

0.5% FSO-100 (DuPont) as wetting agent

Balance water

Every potential user will, however, adapt the composition of the micro-emulsion to the external circumstances, depending on the field of use. In this connection, the following indications may be of use:

a) Influence of the content of water

On horizontal surfaces, in case of an extremely high water content, corresponding to fewer organic components, a decrease in the efficiency may take place. In the case of vertical surfaces, the wetting properties or the contact surface of the micelles of the micro-emulsion may affect the efficiency to an increased extent.

b) Influence of the content of 1-hexanol

Investigations show that the 1-hexanol plays the active role in the extraction of the warfare agents.

c) Influence of the content of n-dodecane

Variation of the content of n-dodecane does not have any substantial effect on the efficiency of the micro-emulsion.

d) Influence of the content of SDS

A better wetting power makes itself positively noticeable, particularly in the case of vertical surfaces. Therefore, the action, for instance, of the SDS is also increased by addition of a wetting agent such as, for instance FSO-100, a typical wetting agent of the so-called zonyl family.

The sensitivity of the micro-emulsion to freezing due to its high water content can, as stated above, be compensated for by the addition of antifreeze agents and $CaCl_2$ or NaCl in order to reduce the freezing point to about −10° C. or, in the extreme case, −20° C., so that a better resistance to freezing is obtained, which also permits the use of the micro-emulsion in the Scandinavian countries. A typical formulation which can be used down to about −10° C. is:

n-dodecane 0.65%

SDS (emulsifier) 1.94%

1-hexanol (co-emulsifier) 2.68%

FSO-100 (wetting agent) 0.46%

NaCl 3.5%

TX-100 (wetting agent) 4.0%

Water Balance

A further improvement in the resistance to freezing can be obtained by additional "antifreeze components". However, it should not be forgotten in this connection that each decrease in the temperature slows down the decontamination process; this applies, however, also to chemical decontamination processes.

Variation of the specific individual components makes it possible to use the micro-emulsion used in accordance with the decontamination process of the invention within a temperature range of −20° C. to +50° C.

The production of the micro-emulsion under field conditions is extremely simple, since for 1000 liters of micro-emulsion, only 50 to 60 liters of mixture of the non-aqueous components need be carried along. No special demands are made on the water; even water from ponds is suitable. Salt-containing water such as, for instance sea water is also suitable for use. The high water content of the emulsion means only a small stock of products, which products are furthermore unobjectionable.

Due to the unobjectionable nature of the products, detoxifications of personnel and materials can be effected for training purposes without any problems.

Since the micro-emulsion is non-toxic, it is possible, for instance, to decontaminate persons wearing contaminated impermeable protective clothing before undressing. This is not possible with traditional methods. However, the use in accordance with the invention of the micro-emulsion goes far beyond the uses mentioned up to now. Due to its non-toxic nature, the micro-emulsion is not only suitable for the "washing-down" of contaminated persons, but it has surprisingly been found that the micro-emulsion used in accordance with the invention is capable of extracting warfare substances from the skin, i.e. the micro-emulsion is capable of removing chemical warfare substances which are present on the skin or which have penetrated below the surface into the skin.

From investigations carried out at institutes which are concerned with chemical warfare agents (for instance, the Prins Maurits Laboratorium TNO, in Rijswijk, Netherlands), it is known that the skin of man differs only slightly from that of the guinea pig in its behavior with respect to chemical warfare agents, especially with respect to their penetration. There were arranged on the skin diffusion cells from which the warfare agent diffused to the skin. It was found later that pigs' ears from slaughter houses are also excellently suitable for investigations in vitro.

For the extracting of the warfare substance from the skin, a micro-emulsion of the following composition 8.4 g sodium lauryl sulfate 11.6 g 1-hexanol 2.8 g n-dodecane 377 g water was used in the test described below.

In this connection, it is to be noted that this formulation is to be considered merely as an example and not as a limitation, and can undoubtedly vary—in the same way as the micro-emulsion used for the decontamination of apparatus and material—within relatively wide limits and be adapted to external factors (for instance, temperature).

The pigs' ears were cleaned; the skin was then removed and stretched out in strips of 2×6 cm on a cork plate covered with aluminum foil. Each of these strips of skin were wetted with 4×1 µl of warfare substance, which corresponds to the NATO load (1 mg/cm$^2$). The warfare substances contained radioisotopes for their quantitative determination, namely:
Lewisite: $^{14}$C
Mustard gas (yperite): $^{35}$S
VX: $^{35}$S The time of action was 4 minutes and 30 minutes. In order to be able to compare the effectiveness of the micro-emulsion for the decontamination with methods used today, parallel tests were carried out with the decontamination powder of the Netherlands armed forces (hereinafter called Dutch powder). The decontamination with the use of the micro-emulsion (ME) was carried out as follows: After the exposure time of 4 hours and 30 minutes, the place wetted with the warfare agent was scrubbed for 30 seconds with hydrophilic rag of bandaging material which had been immersed in 20 cc of micro-emulsion; the excess liquid was then removed with a dry rag. The decontamination with the decontamination powder was effected as follows: After the exposure time of 4 hours and 30 minutes, the exposed place was covered with about 200 mg of powder and rubbed into the skin with a rag of bandaging material for 30 seconds. The powder was then removed insofar as possible with a new rag. Finally, for comparison purposes, strips of skin were wetted with warfare agents, but not decontaminated. All samples of skin were dissolved completely, and warfare agent still present was determined radiochemically (Packard Minaxi Tri-Carb 4000 series). The results are set forth in Table 1:

TABLE 1

| Warfare agent & Exposure time | | % Warfare agent present | | |
|---|---|---|---|---|
| | | Without decontamination | Decontamination with | |
| | | | ME | Dutch Powder |
| Lewisite | 4 min | 100 | 4 ± 2 | 10 ± 2 |
| | 30 min | 100 | 26 ± 8 | 37 ± 9 |
| Mustard Gas | 4 min | 100 | 0.5 ± 0.2 | 4 ± 3 |
| | 30 min | 100 | 0.6 ± 0.2 | 5 ± 5 |
| VX | 4 min | 100 | 1.6 ± 0.2 | 6.1 ± 1.3 |
| | 30 min | 100 | 3.3 ± 1.1 | 9 ± 3 |

It is clear from the table that the micro-emulsion is definitely superior to the Dutch decontamination powder. On the basis of earlier studies, it can be considered proven that the findings are also valid for human skin.

The micro-emulsion used in accordance with the invention is, however, intended not only for the decontaminating of the skin but also for the detoxification of materials, apparatus and weapons systems. While, however, the conventional, aggressive decontaminating agents cannot be used for sensitive devices or airplanes and, for instance, cause damage on electronic devices, detoxification can be carried out without objection here with the micro-emulsion.

In order to be able to extract the warfare substances with the micro-emulsion, a certain time of contact is necessary, which depends on the material to be decontaminated, the depth of penetration, etc. Comparison tests with chemical methods have shown (see subsequent remarks) that the required time of action must, however, be rather similar. This is not surprising since the first step in all methods, namely the extraction, is the factor which is determinative of the speed. The required contact time can be obtained by repeated spraying, or else by increasing the viscosity (addition of a smaller amount of water). The latter is necessary, or at least useful, in particular upon the detoxification of smooth, vertical or oblique surfaces.

The material to be decontaminated ordinarily has a covering having a base of alkyd resins or polyurethanes. Warfare agents penetrate into the layer of paint. In order to be able to compare the decontamination method of the invention which used the micro-emulsion with the chemical decontamination methods which are used today, therefore, in the application comparative tests, plates of steel were coated with alkyd or polyurethane paint and, after hardening, contaminated with sulfuric mustard gas and VX (10 g/m$^2$). The contaminated plates were covered with a Teflon plate in order to make optimal use of the penetration time (3 hours). The plates were then decontaminated both in horizontal position and in vertical position (time of action: 30 minutes). After decontamination, the plates were extracted for 24 hours with a mixture of hexane and isopropyl alcohol and the warfare agents in the extract determined by gas chromatography.

The results are set forth in Table 2.

TABLE 2:

Comparison of conventional methods with the micro-emulsion:

Test plate: Metal with alkyd paint
Warfare agent: Sulfuric mustard gas (a) and VX (b),
in each case 10 g/m$^2$.
Time of action: 3 hours

| Method | Effectiveness % | |
|---|---|---|
| | horizontal | vertical |
| Calcium chloride bleach | (a) 65 | (a) 62 |
| | (b) 96.8 | (b) 90.1 |
| C-8 Emulsion | (a) 88 | (a) 84 |
| | (b) 99.1 | (b) 99.4 |
| Micro-emulsion | (a) 93 | (a) 70 |
| | (b) 99.8 | (b) 96.3 |

These good test results confirm the high efficiency of the micro-emulsion used for the decontaminating of different materials contaminated with chemical warfare agents.

The warfare agents are, to be sure, not destroyed immediately upon the decontamination process of the invention but remain until their hydrolytic degradation in the ground. As an alternative, there is furthermore the possibility of collecting the discharging emulsion in containers and destroying it there by agents traditional for this purpose (for instance, with calcium chloride).

The small amounts of non-dangerous products to be stored are a decisive advantage when logistics are taken into account. Since there are concerned products which are compatible with the environment, no consequential damage need be feared in the case of accidents (leaks) and training. Since the micro-emulsion is not aggressive, sensitive systems and even persons can be detoxified. Here, the chemical detoxification methods are undoubtedly at a disadvantage.

As compared with traditional methods, the system is environmentally friendly, non-aggressive or non-etching-corrosive, easy to handle, and considerably simplified for storage. Since only relatively small amounts of a single previously prepared solution are required and the added water need not be of any particular degree of purity, logistic problems are greatly reduced. It is worthy of note that, due to its non-toxic nature, the micro-emulsion can be used for the decontaminating of chemical warfare agents which adhere to the skin as well as ones which penetrate on the surface into the skin. The astonishing feature, and one which was not foreseeable by the person skilled in the art, is furthermore the finding that by the decontamination process of the invention, the warfare agents are extracted even from layers of paint by the micro-emulsion and that not merely poisons present on the surface can be washed away. These properties make the use of the micro-emulsion so valuable and remarkable.

What is claimed is:

1. A process for decontaminating a substrate contaminated with chemical warfare agents, comprising the steps of: treating the contaminated substrate by one of extracting and washing off with a microemulsion containing 0.1 to 3.5% of a $C_8$–$C_{14}$ alkane; 0.5 to 4.0% of an anionic surfactant; 0.5 to 7.0% of an aliphatic $C_3$–$C_{10}$ alcohol; and the balance being water.

2. The process according to claim 1, wherein the $C_8$–$C_{14}$ alkane is n-dodecane.

3. The process according to claim 1, wherein the anionic surfactant is the alkali salt of a fatty acid or of a sulfonated hydrocarbon.

4. The process according to claim 3, wherein the anionic surfactant is sodium lauryl sulfate.

5. The process according to claim 1, wherein the aliphatic $C_3$–$C_{10}$ alcohol is 1-hexanol.

6. The process according to claim 1, additionally comprising the step of adding to the microemulsion 0.1 to 6.0% of one or more wetting agents.

7. The process according to claim 1, additionally comprising the step of adding to the microemulsion an antifreeze agent.

8. The process according to claim 1, additionally comprising adding to the microemulsion a compound selected from the group consisting of sodium chloride and calcium chloride.

9. The process according to claim 1, wherein the substrate is treated with the microemulsion at a temperature of between −20° C. to +55° C.

10. The process according to claim 1, wherein the microemulsion is hypochlorite free, neutral and non-oxidizing.

11. A hypochlorite-free microemulsion comprising:

a) 0.1 to 3.5% of a $C_8$–$C_{14}$ alkane;

b) 0.5 to 4.0% of an anionic surfactant;

c) 0.5 to 7.0% of an aliphatic $C_3$–$C_{10}$ alcohol;

d) the balance being water.

12. The microemulsion according to claim 11, wherein the $C_8$–$C_{14}$ alkane is n-dodecane.

13. The microemulsion according to claim 11, wherein the anionic surfactant is sodium lauryl sulfate.

14. The microemulsion according to claim 11, wherein the aliphatic $C_3$–$C_{10}$ alcohol is 1-hexanol.

* * * * *